April 12, 1960 D. W. WHITE Plant Pat. 1,933
GLADIOLUS PLANT
Filed June 29, 1959
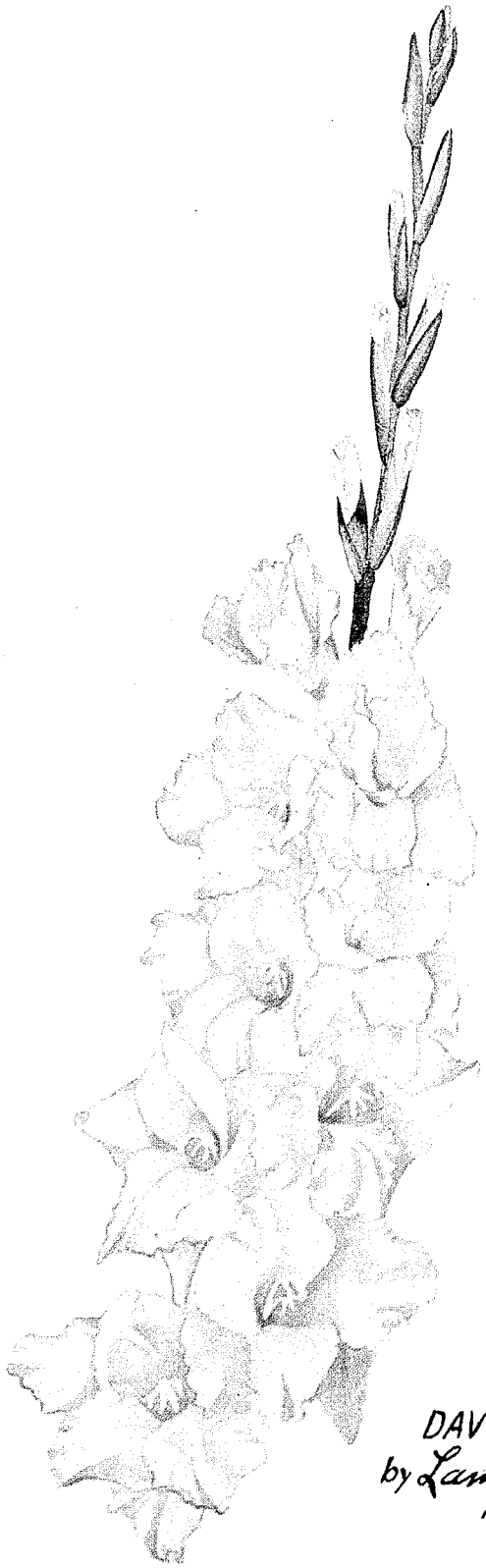
INVENTOR
DAVID WALTER WHITE
by Lamont Johnston
ATTORNEY United States Patent Office Plant Pat. 1,933
Patented Apr. 12, 1960

1,933

GLADIOLUS PLANT

David Walter White, St. Therese, Quebec, Ontario, Canada, assignor to Selected Glads, Inc., New Albany, Ind., a corporation of Tennessee Application June 29, 1959, Serial No. 823,790

1 Claim. (Cl. 47—60)

My present invention relates to a new and improved variety of gladiolus and is notable particularly for its size, smooth color, and inflorescence. I have identified this new variety as seedling No. 507,413 in my breeding work.

To the best of my knowledge this new variety is the result of a cross between the varieties Elizabeth the Queen (unpatented) and a yellow seedling (unpatented). Elizabeth the Queen is the seed parent and the seedling is the pollen parent. Hand pollination was done by me in my field at St. Therese, Quebec, Canada but no precaution was taken to prevent admixture by other varieties by bees or insects.

This new variety has been asexually reproduced by me in the Province of Quebec by natural increase from cormels through several generations and its characteristics have propen to be permanently fixed.

The illustration, made a part of this application, shows a single bloom spike of this new variety and is as nearly true to color as it is possible to depict. The illustration shows the shape and symmetry of the spike as well as the smooth coloring and distinctive form. The illustration is of course greatly reduced.

In the following detailed description, color references indicate "Horticultural Colour Chart" by the British Colour Council. Where there are other references to color, the ordinary dictionary meanings of the terms are intended.

*The plant*

Growth: Very vigorous; very tall, usually attaining a height of 60–64 inches. Propagation is average.

Blooming: Each spike generally has a total of 20 to 22 buds and flowers with 10 to 14 florets being open at once. This variety will bloom in about 85 days from date planted from large bulbs.

Foliage: Deep green. Unusually tall, large plane. Six or seven leaves. Upright; 24 to 30 inches high. Average leaf 2 inches wide.

Stems: Unusually straight and wiry. Diameter at base is from ½ to ¾ inches.

Disease resistance: This variety has been found unusually resistant to Fusarium yellows, Sclerotina dry rot and Septoria leaf spot, to which diseases some other varieties in my fields have been subject, observed when grown as a seedling under irrigation in a black loam soil in the vicinity of St. Therese, Quebec, Canada, under the natural conditions provided by the climate of that area. At the end of the season, it would be found that many other varieties and seedlings had succumbed or been badly affected by the various diseases, whereas this variety remained healthy and unaffected.

Corms: This variety produces large, very smooth bulbs. The husks are the color of dried corn husks and the flesh is Lemon Yellow 4/3.

*The flower*

Spike: Long, has 20–24 buds of which 4–5 open the first day, following which 7 to 9 open the second day and 10–14 the third day. 7 to 8 buds will show color at one time.

Bud: Opening buds are 2½ to 2¾ inches long.

Arrangement: Flowers are formally placed in a double row on the stem and usually all face forward.

Size: Individual florets are exceptionally large, usually measuring six inches across. Upper blooms are progressively smaller.

Form: Flowers are wide-open, recurved and some petals are rolled back so that the tips come to a point. Edges of petals are ruffled.

Petal size: The outer petals are 1¾ inches to 2½ inches in diameter and the inner petals are 1¼ to 2 inches in diameter.

Substance: Heavy; surface smooth with some petals creased at the center toward the tips.

Fragrance: None.

Color: The color in the British Horticultural Colour Chart which most closely resembles my variety is Mimosa Yellow 602/3. The color in the throat shades to Barium Yellow 503/2.

Reproductive organs:

*Stamens.*—Faint violet.

*Pistils.*—Cream. They extend about the same distance as the stamens.

*Comparisons*

My new variety resembles Lorelei (unpatented) more than any other known variety but differs from it principally as follows:

(1) My variety is larger and taller than Lorelei.

(2) My variety has more open florets at one time than Lorelei.

(3) My variety has a more graceful form than Lorelei.

(4) My variety has more buds per spike than Lorelei.

(5) My variety has a straighter stem than Lorelei.

(6) My variety has more of a double-row placement.

Having thus disclosed my invention, I claim:

The new variety of gladiolus plant, substantially as herein described and illustrated, characterized by its size, general symmetry and regular placement of its flower, straightness of stem, and many open florets at one time.

No references cited.